(12) United States Patent
Wack

(10) Patent No.: US 8,322,593 B2
(45) Date of Patent: Dec. 4, 2012

(54) METHOD OF WELDING A COMPONENT TO A SHAPE MEMORY ALLOY WORKPIECE WITH PROVISION OF AN EXTRA CUT FOR COMPENSATING THE VARIATIONS OF DIMENSION OF WORKPIECE AND COMPONENT

(75) Inventor: Thilo Wack, Durmersheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/438,330

(22) PCT Filed: Aug. 14, 2007

(86) PCT No.: PCT/EP2007/058416
§ 371 (c)(1),
(2), (4) Date: Feb. 20, 2009

(87) PCT Pub. No.: WO2008/022950
PCT Pub. Date: Feb. 28, 2008

(65) Prior Publication Data
US 2009/0200360 A1 Aug. 13, 2009

(30) Foreign Application Priority Data
Aug. 23, 2006 (GB) .................................. 0616729.0

(51) Int. Cl.
*B23K 28/00* (2006.01)
*A61F 2/06* (2006.01)
(52) U.S. Cl. ...... 228/170; 228/171; 623/1.16; 623/1.18; 623/1.34
(58) Field of Classification Search .................. 228/170, 228/171; 623/1.2, 1.34, 1.13, 1.16, 1.18; 433/173, 176, 201.1
See application file for complete search history.

(56) References Cited

U.S. PATENT DOCUMENTS
5,464,419 A 11/1995 Glastra
(Continued)

FOREIGN PATENT DOCUMENTS
DE 04130431 A1 3/1993
(Continued)

OTHER PUBLICATIONS
Database Wikipedia, Sep. 11, 2007, "Lumen (anatomy)" XP 002453737 abstract.
(Continued)

*Primary Examiner* — Devang R Patel
(74) *Attorney, Agent, or Firm* — Rutan & Tucker, LLP

(57) ABSTRACT

A method of cutting, polishing and then welding together two metallic components (10, 18), in which the respective components (10, 18) are cut to define respective cut surfaces (14, 16) that are to be polished and fitted together, both to define the relative positions of the two components (10, 18) to be fixed by the welding and to provide facing weld surfaces at which the two components (10, 18) can be welded together. The method is characterized by the steps of i) making at least one extra cut (20), to create at least one zone of elastic deformation that deforms when the cut surfaces (14, 16) are fitted together; ii) polishing the cut surfaces (14, 16) before fitting them together; and iii) designing the dimensions of the cut components (10, 18) so that the zones of elastic deformation compensate for the variations of dimensions caused by the polishing step, thereby retaining the capability of the polished cut surfaces (14, 16, 20) to define said component (10, 18) relative positions during the welding step.

17 Claims, 1 Drawing Sheet

U.S. PATENT DOCUMENTS

| | | | |
|---|---|---|---|
| 5,527,353 | A | 6/1996 | Schmitt |
| 5,591,223 | A | 1/1997 | Lock et al. |
| 5,645,532 | A | 7/1997 | Horgan |
| 5,725,572 | A | 3/1998 | Lam et al. |
| 5,741,327 | A | 4/1998 | Frantzen |
| 5,759,192 | A | 6/1998 | Saunders |
| 5,800,511 | A | 9/1998 | Mayer |
| 5,824,042 | A | 10/1998 | Lombardi et al. |
| 5,824,077 | A | 10/1998 | Mayer |
| 5,843,118 | A | 12/1998 | Sepetka et al. |
| 5,858,556 | A | 1/1999 | Eckert et al. |
| 5,861,027 | A | 1/1999 | Trapp |
| 5,868,783 | A | 2/1999 | Tower |
| 6,022,374 | A | 2/2000 | Imran |
| 6,056,187 | A | 5/2000 | Acciai et al. |
| 6,086,611 | A | 7/2000 | Duffy et al. |
| 6,099,561 | A | 8/2000 | Alt |
| 6,174,329 | B1 | 1/2001 | Callol et al. |
| 6,293,966 | B1 | 9/2001 | Frantzen |
| 6,334,871 | B1 | 1/2002 | Dor et al. |
| 6,379,381 | B1 | 4/2002 | Hossainy et al. |
| 6,387,123 | B1 | 5/2002 | Jacobs et al. |
| 6,409,752 | B1 | 6/2002 | Boatman et al. |
| 6,451,047 | B2 | 9/2002 | McCrea et al. |
| 6,471,721 | B1 | 10/2002 | Dang |
| 6,540,777 | B2 | 4/2003 | Stenzel et al. |
| 6,585,757 | B1 | 7/2003 | Callol |
| 6,676,700 | B1 | 1/2004 | Jacobs et al. |
| 6,797,217 | B2 | 9/2004 | McCrea et al. |
| 7,060,093 | B2 | 6/2006 | Dang et al. |
| 7,135,038 | B1 | 11/2006 | Limon |
| 7,175,654 | B2 | 2/2007 | Bonsignore et al. |
| 7,462,190 | B2 | 12/2008 | Lombardi |
| 7,468,071 | B2 | 12/2008 | Edwin et al. |
| 7,479,157 | B2 | 1/2009 | Weber et al. |
| 7,691,461 | B1 | 4/2010 | Prabhu |
| 8,043,364 | B2 | 10/2011 | Lombardi et al. |
| 2002/0138136 | A1 | 9/2002 | Chandresekaran et al. |
| 2002/0193867 | A1 | 12/2002 | Gladdish et al. |
| 2002/0193869 | A1 | 12/2002 | Dang |
| 2003/0135254 | A1 | 7/2003 | Curcio et al. |
| 2003/0144725 | A1* | 7/2003 | Lombardi ............... 623/1.13 |
| 2003/0216807 | A1 | 11/2003 | Jones et al. |
| 2004/0015228 | A1* | 1/2004 | Lombardi et al. ......... 623/1.18 |
| 2004/0015229 | A1 | 1/2004 | Fulkerson et al. |
| 2004/0073291 | A1 | 4/2004 | Brown et al. |
| 2004/0236400 | A1 | 11/2004 | Edwin et al. |
| 2004/0236409 | A1 | 11/2004 | Pelton et al. |
| 2004/0254637 | A1 | 12/2004 | Yang et al. |
| 2005/0049682 | A1 | 3/2005 | Leanna et al. |
| 2005/0060025 | A1* | 3/2005 | Mackiewicz et al. ........ 623/1.34 |
| 2005/0172471 | A1 | 8/2005 | Vietmeier |
| 2005/0278019 | A1 | 12/2005 | Gregorich |
| 2006/0216431 | A1 | 9/2006 | Kerrigan |
| 2006/0241741 | A1 | 10/2006 | Lootz |
| 2006/0265049 | A1 | 11/2006 | Gray et al. |
| 2007/0219624 | A1 | 9/2007 | Brown et al. |
| 2008/0051885 | A1 | 2/2008 | Llanos et al. |
| 2008/0188924 | A1 | 8/2008 | Prabhu |
| 2009/0125092 | A1 | 5/2009 | McCrea et al. |
| 2009/0125099 | A1 | 5/2009 | Weber et al. |
| 2009/0204203 | A1 | 8/2009 | Allen et al. |
| 2010/0070021 | A1 | 3/2010 | Wack et al. |
| 2010/0114298 | A1 | 5/2010 | Dom et al. |
| 2010/0191321 | A1 | 7/2010 | Schlun et al. |
| 2010/0211161 | A1 | 8/2010 | Dreher |
| 2011/0196473 | A1 | 8/2011 | McCrea et al. |
| 2011/0198327 | A1 | 8/2011 | Prabhu |
| 2011/0245905 | A1 | 10/2011 | Weber et al. |
| 2011/0319977 | A1 | 12/2011 | Pandelidis et al. |
| 2012/0041542 | A1 | 2/2012 | Lombardi et al. |

FOREIGN PATENT DOCUMENTS

| | | |
|---|---|---|
| DE | 29621207 U1 | 1/1997 |
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0709068 A2 | 5/1996 |
| EP | 0800800 A1 | 10/1997 |
| EP | 0847733 A1 | 6/1998 |
| EP | 1157673 A2 | 11/2001 |
| EP | 1212991 A2 | 6/2002 |
| EP | 1255507 A1 | 11/2002 |
| EP | 1356789 A1 | 10/2003 |
| EP | 1433438 A2 | 6/2004 |
| EP | 1488763 A2 | 12/2004 |
| FR | 2626046 A1 | 7/1989 |
| GB | 453944 A | 9/1936 |
| JP | 07315147 A | 12/1995 |
| WO | 9503010 A1 | 2/1995 |
| WO | 9733534 A1 | 9/1997 |
| WO | 9915108 A1 | 1/1999 |
| WO | 0064375 A1 | 11/2000 |
| WO | 0158384 A1 | 8/2001 |
| WO | 0215820 A2 | 2/2002 |
| WO | 03101343 A1 | 12/2003 |
| WO | 2004028408 A1 | 4/2004 |
| WO | 2004058384 A1 | 7/2004 |
| WO | 2005072652 A1 | 8/2005 |
| WO | 2006014768 A1 | 2/2006 |
| WO | 2006047977 A1 | 5/2006 |
| WO | 2008006830 A1 | 1/2008 |
| WO | 2008028964 A2 | 3/2008 |
| WO | 2008068279 A1 | 6/2008 |
| WO | 2008101987 A1 | 8/2008 |
| WO | 2009030748 A2 | 3/2009 |

OTHER PUBLICATIONS

International Application No. PCT/EP2001/009467 International Preliminary Examination Report Sep. 17, 2002.

International Application No. PCT/EP2001/009467 International Search Report dated Feb. 18, 2002.

International Application No. PCT/EP2007/057041 filed Jul. 10, 2007 International Preliminary Report on Patentability dated Jan. 13, 2009.

International Application No. PCT/EP2007/057041 filed Jul. 10, 2007 International Search Report dated Oct. 18, 2007.

International Application No. PCT/EP2007/057041 filed Jul. 10, 2007 Written Opinion Jan. 10, 2009.

International Application No. PCT/EP2007/058416 filed Aug. 14, 2007 International Preliminary Report on Patentability dated Feb. 24, 2009.

International Application No. PCT/EP2007/058416 filed Aug. 14, 2007 International Search Report dated Nov. 22, 2007.

International Application No. PCT1EP2007/058416 filed Aug. 14, 2007 Written Opinion dated Feb. 23, 2009.

International Application No. PCT/EP2007/063347 filed Dec. 5, 2007 International Search Report dated Jun. 10, 2009.

International Application No. PCT/EP2007/063347 filed Dec. 5, 2007 Written Opinion dated Jun. 10, 2009.

International Application No. PCT/EP2007/063347 filed on Dec. 5, 2007 International Search Report dated Feb. 4, 2008.

International Application No. PCT/EP2008/052121 filed Feb. 21, 2008 International Preliminary Report on Patentability dated Aug. 26, 2009.

International Application No. PCT/EP2008/052121 filed Feb. 21, 2008 International Search Report dated May 19, 2008.

International Application No. PCT/EP2008/052121 filed Feb. 21, 2008 Written Opinion dated May 9, 2008.

U.S. Appl. No. 10/362,040, filed Jun. 27, 2003 Advisory Action dated Jan. 9, 2009.

U.S. Appl. No. 10/362,040, filed Jun. 27, 2003 Advisory Action dated Nov. 29, 2006.

U.S. Appl. No. 10/362,040, filed Jun. 27, 2003 Office Action dated Aug. 18, 2005.

U.S. Appl. No. 10/362,040, filed Jun. 27, 2003 Office Action dated Aug. 2, 2006.

U.S. Appl. No. 10/362,040, filed Jun. 27, 2003 Office Action dated Dec. 10, 2007.

U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
EP 07802603.6 filed Aug. 14, 2007 Office Action dated Dec. 13, 2010.
U.S. Appl. No. 10/362,040, filed Jun. 27, 2003 Advisory Action dated Dec. 16, 2010.
U.S. Appl. No. 12/373,116, filed Jul. 14, 2009 Non-Final Office Action dated Nov. 10, 2010.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 12/373,116, filed Jul. 14, 2009 Advisory Action dated Jul. 26, 2011.
U.S. Appl. No. 12/373,116, filed Jul. 14, 2009 Final Office Action dated Apr. 27, 2011.
U.S. Appl. No. 12/517,096, filed Jun. 1, 2009 Office Action dated May 6, 2011.
EP 07787316.4 filed Jul. 10, 2007 Examination Report dated Dec. 23, 2011.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 18, 2011.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.

* cited by examiner

METHOD OF WELDING A COMPONENT TO A SHAPE MEMORY ALLOY WORKPIECE WITH PROVISION OF AN EXTRA CUT FOR COMPENSATING THE VARIATIONS OF DIMENSION OF WORKPIECE AND COMPONENT

PRIORITY

This application is a U.S. national stage application under 35 USC §371 of International Application No. PCT/EP2007/058416, filed Aug. 14, 2007, claiming priority to United Kingdom Patent Application No. 0616729.0, filed Aug. 23, 2006, each of which is incorporated by reference in its entirety into this application.

TECHNICAL FIELD

This invention relates to a method of cutting, polishing and then welding together two metallic components, in which the respective components are cut to define respective cut surfaces that are to be polished and fitted together, both to define the relative positions of the two components to be fixed by the welding and provide facing weld surfaces at which the two components can be welded together.

BACKGROUND ART

Applicant makes self-expanding stents from nickel titanium shape memory alloy. The material is not particularly radiopaque and so stents made of it are usually provided with one or more radiopaque markers. Tantalum is an attractive material not only because it is biocompatible but also because it is close to the nickel titanium alloy in electrochemical potential and so resists galvanic corrosion after placement in the body. Furthermore, the two metals can be reliably welded together.

Applicant's WO 02/15820 discloses a particularly attractive form of radiopaque marker. When the self-expanding stent is radially compressed within a sheath in a delivery catheter system, the "ring of spoons" at each end of the stent, that serve as the tantalum markers, form a virtually complete ring of tantalum and so are relatively strongly visible to the radiographer.

An elegant aspect of the welding method taught in WO 02/15820 is that no jig or clamp is needed, to hold the two component parts in the desired relative positions for welding. Instead, the two components engage with each other in a mechanically interfering "form fit" ready for welding. Given the small size of the component, this is a distinct advantage.

Applicant's further published application, WO 01/58384 A1, discloses an elongate stent, preferably an oesophageal stent. A plurality of radiopaque beads are mounted onto selected ones of the uncovered extremities at the end or ends of the stent. In one embodiment, each bead has a throughbore which receives a spigot formed at the stent extremity. The spigots are each defined by two parallel resilient fingers formed out of an extension of the stent material. The two fingers are separated by a slit which allows the fingers to approximate for insertion along the throughbore, then to resiliently separate. Barbed tips are provided at the ends of the fingers to resist reverse movement of the fingers through the throughbore after they have emerged from the bead throughbore and again separated, thereby holding each bead on its spigot. To secure the beads, they are welded onto the spigots.

Stent components must be polished before they are placed in the body, and the rate of chemical polishing (in particular electrochemical polishing) of nickel titanium alloy can be very different from that of tantalum. This would indicate polishing separately the tantalum markers and the nickel titanium stent, but the chemical polishing process can disturb the accurate dimensional tolerance as achieved when these components are cut with a laser. One does not know with certainty how much material will have been removed from the intended welding interface by the chemical polishing procedures. Once the dimensions are disturbed, the certainty of optimal welding between the nickel titanium and the tantalum, at the welding interface, can be prejudiced, one desires to polish separately, then weld together with high precision and complete certainty.

Another publication, US 2005/0172471 A1, discloses how the change of nitinol between the austenite and martensite phases at the transition temperature can be used to encapsulate a marker element within a loop of shape memory alloy, with the loop contracting to engage the marker element in an interference fit due to the phase change. The principle is similar to thermo-mechanical interference fit techniques often used for joining, e.g., two metal components where one fits inside a loop or hole of the other, and relies on the shape change properties of the shape memory alloy at the transition point.

DISCLOSURE OF INVENTION

The present invention is defined in claim 1 below. The dependent claims are directed to optimal and preferred features.

The present inventor has had the insight that one can use the elastic deformation behaviour of martensitic nickel titanium shape memory alloy to achieve more certainty of location at the welding interface. Nickel titanium shape memory alloy can accommodate remarkably large amounts of strain without adverse effect on the mechanical properties (especially fatigue performance) of the finished stent product. The elastic deformation of nitinol is often referred to as "superelastic" or "pseudo-" elastic deformation, which is considered herein as a form of elastic deformation.

Thus, the essence of the present invention is to accommodate dimensional variations at the welding interface with elastic mechanical strain within the workpiece. In this context, the large (pseudo-) elastic (or superelastic) strains achievable with nitinol are especially useful as one can accommodate relatively large variations in the dimensions of the components to be welded as compared with the modest elastic strains achievable with, say, commonly-used medical grade stainless steels.

Typically, in preparing the workpiece for welding, one would provide a slit in the workpiece, remote from the intended welding interface yet close enough to the interface to allow portions of the workpiece that flank the slit to move towards each other, thereby narrowing the slit, to provide all the strain that is needed to achieve the desired welding interface.

The invention is particularly attractive in the context of a weld interface between the shape memory alloy workpiece and a metallic component that is to be welded to the workpiece, which has a recess in which a portion of the workpiece is received, with the welding interface corresponding to a portion at least at the periphery of the recess. Providing one or more slits within the workpiece, within the periphery of the recess, or in a neck portion of the workpiece crossing the periphery of the recess, can provide the strain that will help to provide a consistent interaction between the workpiece and the metallic component, that will in turn allow precise and reliable welding at the weld interface, and all this without any help from any tooling, jig or other holding fixture to maintain the correct relative positions of the weld surfaces.

BRIEF DESCRIPTION OF DRAWINGS

For a better understanding of the present invention, and to show more clearly how the same may be carried into effect, reference will now be made, by way of example, to the accompanying drawings, in which:

Each of FIGS. 1 to 6 is a plan-view of a detail of a nickel titanium shape memory alloy stent, showing a welding interface between a portion of that stent and a radiopaque marker element.

BEST MODE FOR CARRYING OUT THE INVENTION

Figure 1:
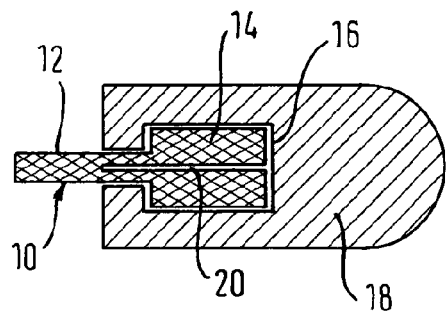

We refer first to FIG. 1. What is shown is recognisably equivalent to the welding interface in WO 02/15820, between a projection at one end of the stent and a "spoon" of tantalum that surrounds the projection and is welded to it. Thus, in FIG. 1, the nickel titanium shape memory alloy stent 10 has at each end (not shown) a plurality of spigots 12, each of which extends like a neck into a head portion 14 that is received in a recess 16 formed in a "spoon" 18 of tantalum metal. Typically, each spoon represents ¼ of the circumference of a tube of tantalum having the same radius as the tube of nickel titanium alloy raw material from which the stent matrix is cut by a laser. See WO 02/15820 for more information.

The intended welding interface is at the periphery of the recess 16, the intention being that weld metal from the components themselves should fill the small gap between the periphery of the recess 16 and the periphery of the head portion 14 within it. Nevertheless, it is also envisaged that welding filler material may be used, whenever circumstances indicate its usefulness.

Laser cutting of the nickel titanium stent and the tantalum spoon can be very accurate but, when the stent and spoon are separately polished electro-chemically before being brought together, there can be a degree of uncertainty as to the precise dimensions of the recess 16 and the head portion 14. The present invention provides a solution to that difficulty.

On FIG. 1, it can be seen that there is a long slot (otherwise called "slit") 20 that divides the head portion 14 into two separate side portions spaced from each other by the width of the slot 20. With all the other laser cutting that the nickel titanium workpiece suffers, in the preparation of the stent strut matrix, it is a trivial further step for the laser to cut the additional slot 20.

Now, if the overall width of the head portion 14 is made deliberately just slightly larger than the width which is optimal to occupy the recess 16 then, without the presence of the slit 20, it would not be possible to get the head portion 14 into the recess 16 (unless electro-chemical polishing of the head portion 14 had been somewhat more aggressive than anticipated). However, if we make the dimensions of the head portion 14 slightly larger, and appropriate for the case when electro-chemical polishing of the head portion 14 is at its most aggressive then, at all other times, when electro-chemical polishing of the head portion 14 is not quite so aggressive, the "over-size" of the head portion 14 after polishing is nevertheless still able to be accommodated within the recess 16, simply by some degree of approximation (coming together) of the flanks of the slot 20. In other words, to get the head portion 14 into the recess 16, the slot gets a little narrower.

As explained above, the strain suffered by nickel titanium material within the spigot 12 or the head portion 14, when the slot 20 suffers a degree of narrowing, is strain that is accommodated either by movement of twin boundaries within the martensitic material, or by transformation of austenite to stress-induced martensite (depending on the temperature of the material during deformation) and is not detrimental to the mechanical properties of performance of the stent after manufacture.

Nickel titanium shape memory alloy is remarkable enough already, with its biological compatibility, and martensitic/austenitic phase transformation compatible with the interval between room temperature and body temperature. This additional pseudo-elastic strain capability of nickel titanium alloy, in order to enhance the certainty of welding to it of radiopaque marker portions of a different metal, is yet another helpful property that this material exhibits.

Figure 2:
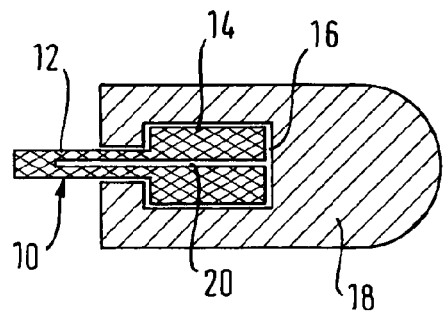

Moving on to FIG. 2, all components correspond but the slot 20 has been made longer in order to deliver a somewhat different distribution of strain within the nickel titanium alloy component.

Figure 3:
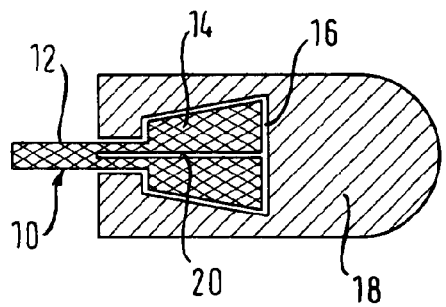

FIG. 3 represents another variation. This time, the slot 20 is not different form that of the FIG. 1 embodiment but the periphery of the head portion 14 is a trapezium rather than a rectangle. Readers will appreciate that optimising behaviour at the welding interface can involve careful harmonising of weld interface shape and slot dimensions, with the aim of achieving an optimal face-to-face relationship between the two components at the welding interface, all the way along the length of the welding interface.

Figure 4:
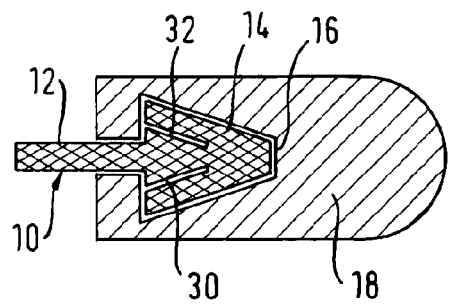

This theme is developed one step further in the embodiment of FIG. 4 in which we find an arrowhead shape for the head portion 14, that portion exhibiting not one but two slots 30 and 32, symmetrically one each side of the centreline of the arrowhead. Again, optimal face-to-face relationship between the components all the way around the welding interface can be achieved by complementary arrangement and disposition of the slots that allow the requisite strain to be provided and accommodated within the nickel titanium workpiece.

Figure 5:
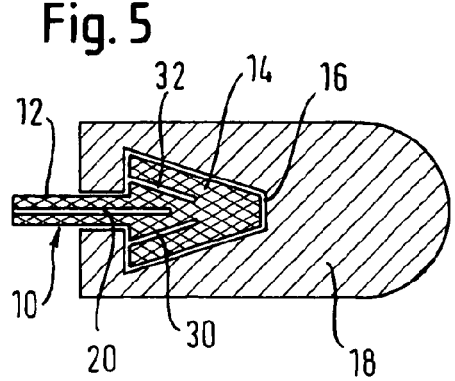

FIG. 5 exhibits three slots in what can be seen as a form of combination of the embodiments of the earlier Figures.

Figure 6:
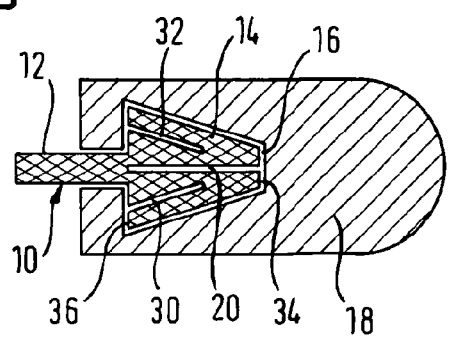

Finally, FIG. 6 closely resembles the FIG. 4 embodiment, but with a centreline slot 20 that extends all the way to the tip 34 of the arrowhead. Thus, slot 20 accommodates squeeze at the arrowhead tip 34 whereas the pair of slots 30, 32 can accommodate squeeze at the base 36 of the arrowhead.

The expertise of the present inventor is stent manufacture. However, nickel titanium shape memory alloy is important in many other fields where dimensional tolerances are of decisive importance, and where components of other metals need to be welded to nickel titanium alloy product. One area that comes to mind is in the field of dentistry. Readers will appreciate that the particular way in which the large pseudo-elastic strain that shape memory alloy can exhibit will be used to optimise weld interface presentation will be highly dependent on the specific form of the two component portions to be welded together. What is shown in the accompanying drawings is intended to be just one example of application of an inventive concept which clearly has very wide application. Specifically, the invention is applicable to stents of biocompatible materials other than nickel titanium alloy, notably stainless steel. With any material other than a superelastic or pseudo-elastic alloy (a property common to many shape memory alloys), one has to rely on the design of the components to accommodate any variations, as the materials themselves are typically only able to achieve elastic strains of about 3% or less.

Other embodiments should be mentioned, for the sake of completeness.

A stent is typically designed to be formed as a pattern of adjacent rings of undulations, which are bridged together to form an essentially tubular structure where undulations are embodied in the form of zig-zag struts, the zig-zag struts may include a bridged repeating pattern made of a unit of four generally linear members that extend oblique to the longitudinal axis to intersect each other at three apices spaced apart circumferentially and axially (like a letter 'M' or 'W'). Also, the prosthesis can utilize not only the circumferential bridges but also other bridge configurations in combination. Alternatively, the bridge directly connects a peak of one circumferential section to another peak of an adjacent circumferential section. In yet another alternative, the bridge may connect a peak of one circumferential section to a trough of an adjacent circumferential section. In a further alternative, the bridge can connect a trough of one circumferential section to a trough of an adjacent circumferential section. Moreover, the undulations can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths. In one form, a continuous zig-zag string may be wound as a helical coil, with intermittent bridging connections between successive turns of the coil, achieving similar effects. And as used herein, the term "implantable prosthesis" is intended to cover not only a bare stent but also coated, covered, encapsulated, bioresorbable stent or any portion of similar stents.

Bio-active agents can be added to the prosthesis (e.g., either by a coating or via a carrier medium such as resorbable polymers) for delivery to the holt's vessel or duct. The bio-active agents may also be used to coat the entire stent. A material forming the stent or coupled to the stent may include one or more (a) non-genetic therapeutic agents, (b) genetic materials, (c) cells and combinations thereof with (d) other polymeric materials.

(a) Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

(b) Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BlVfiP-2, BMP-3, BMP-4, BMP-5, BMP-6 (Vgr-1), BMP-7 (OP-1), BMP-S, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA"s encoding them.

(c) Cells can be of human origin (autologous or allogeneic) or from an animal source (xenogeneic) genetically engineered if desired to deliver proteins of interest at the deployment site. The cells may be provided in a delivery media. The delivery media may be formulated as needed to maintain cell function and viability.

(d) Suitable polymer materials as a coating or the base material may include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

Industrial Applicability

The present invention is applicable to industrial manufacturing processes in which two metallic components are to be welded together; in particular, the invention finds application in the manufacture of a shape memory alloy workpiece, such as a stent, to which a component is to be welded, such as a tantalum marker.

The invention claimed is:

1. A method of cutting, polishing and then welding together first and second metallic components, in which the respective components are cut to define respective cut surfaces that are to be polished and fitted together, both to define the relative positions of the two components to be fixed by the welding and to provide facing weld surfaces at which the two components can be welded together, the method comprising:
   i) making a centerline slot along a centerline of the first component, and making a first short slot and a second short slot symmetrically one on each side of the centerline of the first component, each of the first and second short slots having a length less than a length of the centerline slot, the centerline slot and first and second short slots together dividing a portion of the first component into a plurality of portions and creating at least one zone of elastic deformation that deforms when the cut surfaces are fitted together, wherein the first component is a male component and forms a plug having a head portion extending from a stem portion, with the head portion including at least a portion of the centerline slot and being wider than the stem portion, and wherein the second component is a female component defining a socket having a channel portion into which the stem portion is received and a recess portion into which the head portion is received, the recess portion having substantially the same shape as the head portion;
   ii) polishing the cut surfaces before fitting them together;
   iii) welding the polished cut surfaces together, wherein the zone of elastic deformation compensates for variations of dimensions at the welding interface and provides the strain that will maintain the correct relative positions of respective components during welding.

2. The method according to claim 1, wherein one of the components is a strut matrix of a stent and the other comprises a radiopaque marker of the stent.

3. The method according to claim 2, wherein each of the two components is formed from a tube of substantially the same diameter, and the welding step takes place with the two tubes co-linear and engaged, end-to-end.

4. The method according to claim 1, wherein polishing the cut surfaces removes an amount of material from each surface, variable between a minimum and a maximum amount, and the dimensions of the cut components are designed so that:
   i) if the minimum amount of material is removed from both male and female components, the zone of elastic deformation is configured to deform sufficiently to allow the male component to enter the female component, and
   ii) if the maximum amount of material is removed from both the male and female components, the zone of elastic deformation is configured still to deform when the male component enters the female component so as to establish an elastic restoring force for retaining said components in their relative positions.

5. The method according to claim 1, wherein, before polishing, the cut male component is too large to be received in the cut female component.

6. The method according to claim 1, wherein the head of the male component includes the first and second short slots by which zones of elastic deformation are created to compensate for the variations of dimensions.

7. The method according to claim 1, wherein facing weld surfaces are provided along at least one edge surface of the male component and a corresponding edge surface of the female component.

8. The method according to claim 1, wherein the first component that includes the zone of elastic deformation is a component made of a shape memory material.

9. The method according to claim 8, wherein the shape memory material is a nickel-titanium shape memory alloy.

10. A method of cutting, polishing and then welding together first and second metallic components, in which the respective components are cut to define respective cut surfaces that are to be polished and fitted together, both to define the relative positions of the two components to be fixed by the welding and to provide facing weld surfaces at which the two components can be welded together, the method comprising:
   i) making a centerline slot along a centerline of the first component, and making a first short slot and a second short slot symmetrically one on each side of the centerline of the first component, each of the first and second short slots having a length less than a length of the centerline slot, the centerline slot and first and second short slots together dividing a portion of the first component into a plurality of portions and creating at least one zone of elastic deformation that deforms when the cut surfaces are fitted together, each of the two components formed from a tube of substantially the same diameter;
   ii) polishing the cut surfaces before fitting them together;
   iii) welding the first and the second components together when the two tubes are co-linear and engaged, end-to-end; and
   iv) welding the polished cut surfaces together, wherein the zone of elastic deformation compensates for variations of dimensions at the welding interface and provides the strain that will maintain the correct relative positions of respective components during welding.

11. The method according to claim 10, wherein one of the components is a strut matrix of a stent and the other comprises a radiopaque marker of the stent.

12. The method according to claim 11, wherein the first component is a male component and includes the first and second short slots by which zones of elastic deformation are created to compensate for the variations of dimensions.

13. The method according to claim 12, wherein said male component forms a plug having a head portion extending from a stem portion, with the head portion including at least a portion of the centerline slot and being wider than the stem portion, and wherein the second component is a female component defining a socket having a channel portion into which the stem portion is received and a recess portion into which the head portion is received, the recess portion having substantially the same shape as the head portion.

14. A method of cutting, polishing and then welding together first and second metallic components, in which the respective components are cut to define respective cut surfaces that are to be polished and fitted together, both to define the relative positions of the two components to be fixed by the welding and to provide facing weld surfaces at which the two components can be welded together, the method comprising:

i) making a centerline slot along a centerline of the first component, and making a first short slot and a second short slot symmetrically one on each side of the centerline of the first component, each of the first and second short slots having a length less than a length of the centerline slot, the centerline slot and first and second short slots together dividing a portion of the first component into a plurality of portions and creating at least two zones of elastic deformation that deforms when the cut surfaces are fitted together;

ii) polishing the cut surfaces before fitting them together;

iii) welding the polished cut surfaces together, wherein the zones of elastic deformation compensate for variations of dimensions at the welding interface and provide the strain that will maintain the correct relative positions of respective components during welding.

15. The method according to claim 14, wherein one of the components is a strut matrix of a stent and the other comprises a radiopaque marker of the stent.

16. The method according to claim 15, wherein the first component is a male component, and wherein the first and second short slots extend along axes intersecting the centerline of the first component.

17. The method according to claim 16, wherein the centerline slot terminates prior to a closed end of the first component.

* * * * *